United States Patent [19]

Pauly et al.

[11] 4,427,866

[45] Jan. 24, 1984

[54] ROTARY ELECTRICAL COUPLING FOR MICROWAVE HEATING APPARATUS

[75] Inventors: John A. Pauly, Milford; John K. Malinoski, Westboro, both of Mass.

[73] Assignee: Baxter Travenol Laboratories, Inc., Deerfield, Ill.

[21] Appl. No.: 338,637

[22] Filed: Jan. 11, 1982

[30] Foreign Application Priority Data

Dec. 31, 1981 [CH] Switzerland ............................ 393469

[51] Int. Cl.[3] ............................................... H05B 6/68

[52] U.S. Cl. ....................... 219/10.55 B; 219/10.55 R; 219/10.55 F; 374/110; 374/154; 374/166; 340/596

[58] Field of Search .................. 219/10.55 F, 10.55 R, 219/10.55 E, 10.55 B, 10.55 A, 10.55 D, 10.55 M, 483, 486, 487; 374/110, 111, 112, 149, 153, 154, 166; 340/588, 589, 596; 128/214 A, 214 D

[56] References Cited

U.S. PATENT DOCUMENTS

| | | | |
|---|---|---|---|
| 3,154,663 | 10/1964 | Halvorsen | 128/214 A |
| 3,428,772 | 2/1968 | Wallenfels | 219/10.55 |
| 3,494,722 | 2/1970 | Gray | 21/54 |
| 3,626,135 | 12/1971 | Fitzmayer | 219/10.55 |
| 3,676,058 | 7/1972 | Gray | 21/54 R |
| 3,963,892 | 6/1976 | Camph et al. | 219/10.55 M |
| 4,036,995 | 7/1977 | Koether et al. | 340/596 X |
| 4,092,512 | 5/1978 | Suzuki et al. | 219/10.55 F |
| 4,121,078 | 10/1978 | Takano et al. | 219/10.55 F |
| 4,167,663 | 9/1979 | Granzow, Jr. et al. | 128/214 A |
| 4,210,794 | 7/1980 | Oguri | 219/10.55 F |
| 4,233,478 | 11/1980 | Stahl et al. | 219/10.55 B |
| 4,324,138 | 4/1982 | Davis et al. | 374/111 |
| 4,330,696 | 5/1982 | Pomeroy et al. | 219/10.55 F |

FOREIGN PATENT DOCUMENTS

| | | | |
|---|---|---|---|
| 2320440 | 11/1974 | Fed. Rep. of Germany | 219/10.55 R |
| 2366045 | 7/1977 | Fed. Rep. of Germany | 219/10.55 R |
| 2721802 | 11/1977 | Fed. Rep. of Germany | 219/10.55 E |

*Primary Examiner*—B. A. Reynolds
*Assistant Examiner*—Philip H. Leung
*Attorney, Agent, or Firm*—John E. Toupal

[57] ABSTRACT

Disclosed is an electrical connection system for a microwave oven including a chamber defining a housing, a source for transmitting microwave energy into the chamber, a turntable rotatably mounted within the chamber and defining stations for receiving articles to be heated and a drive mechanism for producing rotation of the turntable. A control circuit controls energization of the source in response to signal outputs from temperature responsive sensors positioned in the heating stations. The rotary coupling includes a stationary portion mounted on the housing and having stationary contacts connected to the control circuit and a rotary portion mounted on the turntable and having rotary contacts connected to the sensors and slidably engaging the stationary contacts during rotational movement of the turntable.

12 Claims, 10 Drawing Figures

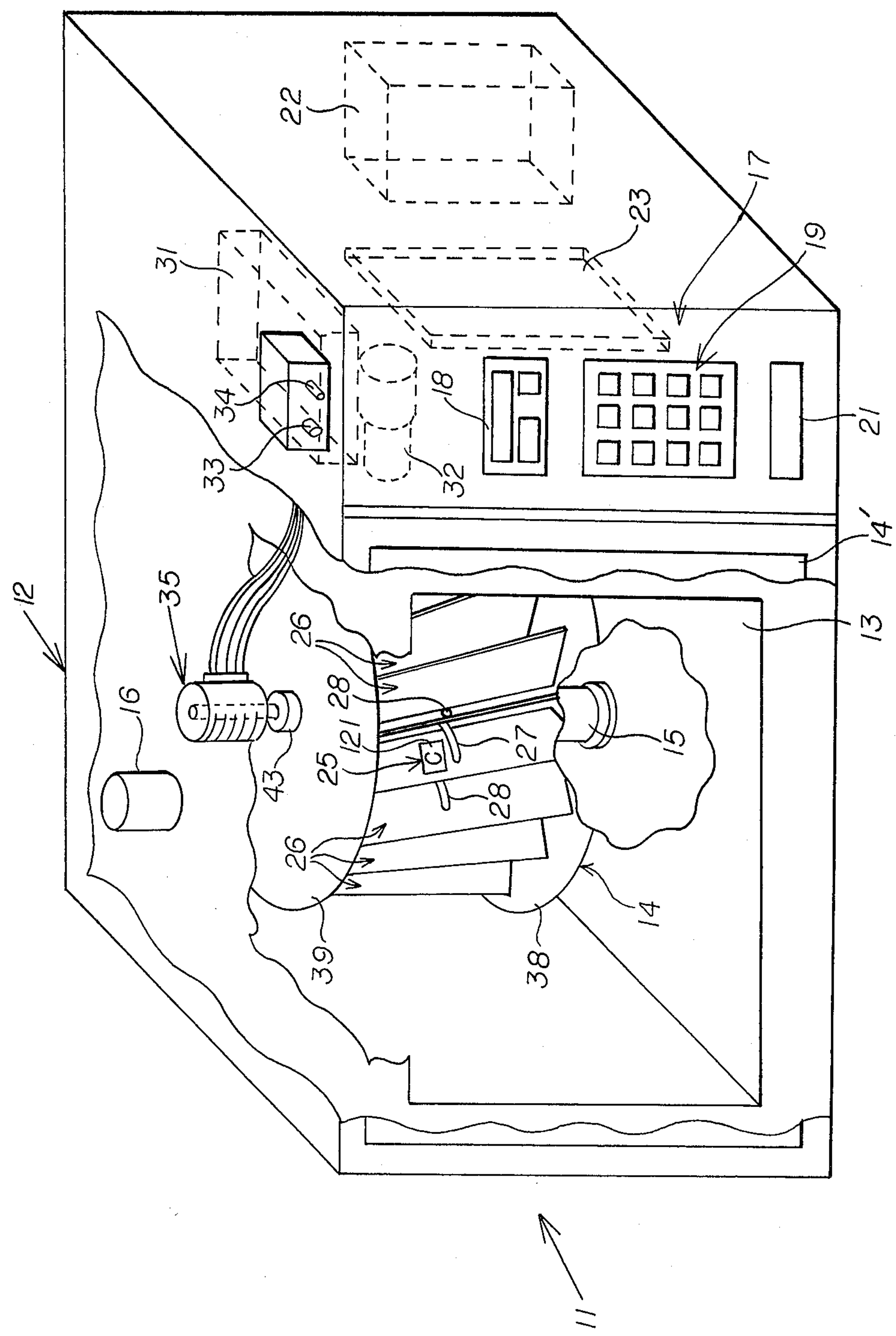
F I G. 1

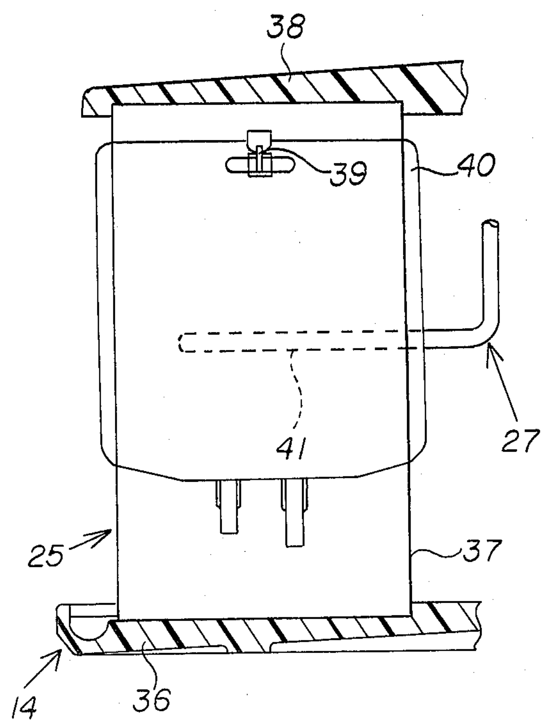
F I G. 2
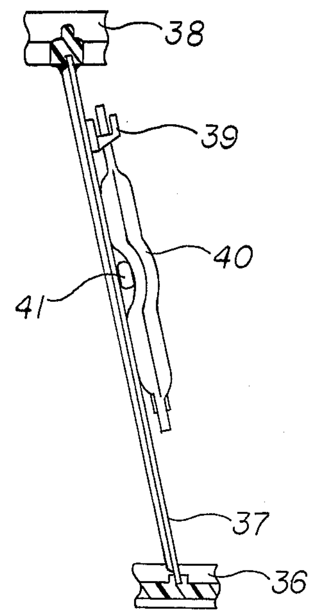
F I G. 3
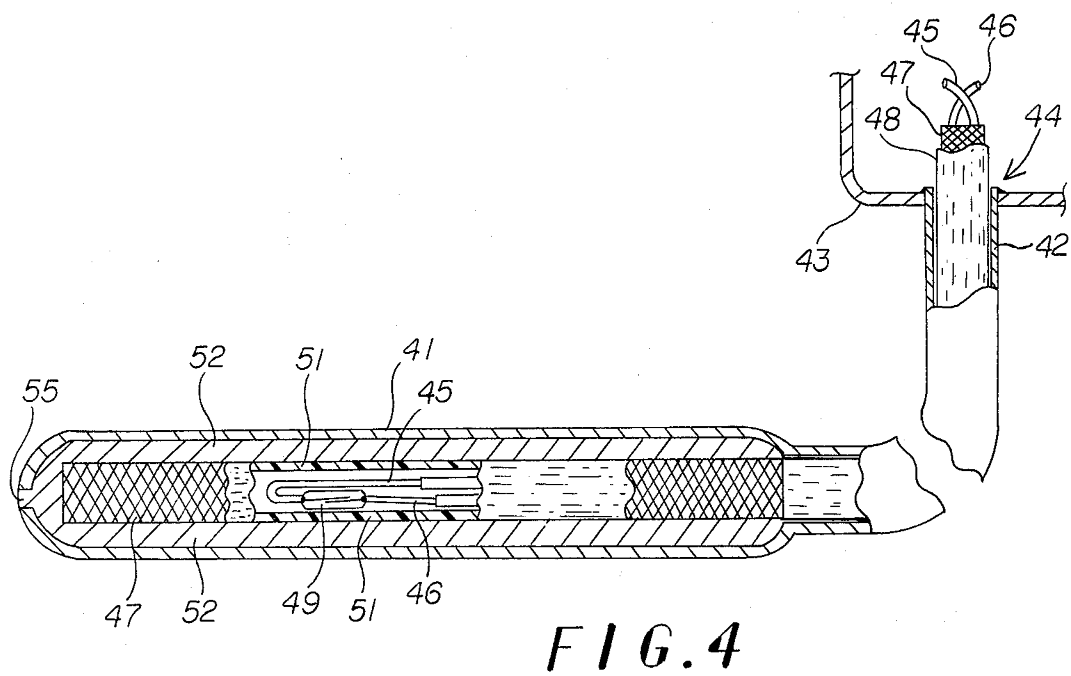
F I G. 4

ROTARY ELECTRICAL COUPLING FOR MICROWAVE HEATING APPARATUS

BACKGROUND OF THE INVENTION

This invention relates generally to microwave apparatus for safely heating a batch of distinct articles and, more specifically, to such an apparatus for thawing the frozen parenteral solution content of plastic bags.

The addition of medication to parenteral solutions is a widely accepted clinical practice. Although many intravenous additives presently are prepared in patient care areas by nursing staff, there is an increasing pressure on hospitals to establish pharmacy admixture programs to minimize medication errors and the risk of microbial contamination. To optimize the use of available manpower, some pharmacies have adopted the practice of freezing admixtures.

It is known that several antibiotics in clinical use are stable for extended periods of time when frozen in large volume parenteral solutions. Indeed, freezing of antibiotic solutions often can prolong stability and suspend growth of essentially any microbial contaminant. Studies have shown that antibiotic admixtures are unharmed for up to 30 days if frozen in 100 or 50 ml. admixture container bags. However, the several hours required for room temperature thawing of these units often make this technique unsuitable in the hospital. Some improvement in preparation efficiency can be achieved by thawing the bags in warm water baths, a technique that is widely practiced in blood banks. Warm water thawing, however, still consumes significant time in addition to requiring labor intensive procedures for both cleaning baths to reduce contamination levels and avoiding contamination by touch during pooling operations.

As a solution to these problems, microwave ovens have been proposed as vehicles for thawing frozen admixtures prior to intravenous administration. The resultant rapid thawing would allow centralized admixture programs to operate a 24-hour service without the need for a pharmacy to be ready to make admixtures at all times. Other attributes would include the opportunity to take advantage of the efficiency accompanying large scale manufacturing techniques. Especially important would be the possibility of introducing pre-release quality control on manufactured lots, presently not possible for admixtures prepared by conventional methods where the maximum permissible refrigerated storage is 24 hours.

Although the efficiency of microwave heating presents many advantages, prior microwave ovens do not satisfy all requirements for safely thawing individually bagged units of parenteral substances on a scale necessary for practical applications. Even the most sophisticated timing and temperature sensing controls available with existing microwave ovens cannot prevent under all conditions the overheating of individual units during batch thawing thereof. For example, the inadvertent combination, in a given batch, of units exhibiting substantially different volumes or chemical characteristics can cause non-uniform temperature increases and resultant overheating of specific units. Similar consequences can derive from inadvertently including a thawed or partially thawed bag with a fully frozen batch. In addition to possibly degrading the therapeutic effectiveness of its content, overheating can cause rupture of an individual bag. Under certain conditions the explosive discharge from a ruptured bag can injure attendant personnel and in all cases must be cleaned from the equipment surface on which it collects.

The object of this invention, therefore, is to provide microwave oven apparatus that can safely, efficiently and simultaneously thaw the frozen parenteral mixture content of multiple plastic bags.

SUMMARY OF THE INVENTION

The invention comprises an electrical connection system for a microwave oven including a chamber defining a housing, a source for transmitting microwave energy into the chamber, a turntable rotatably mounted within the chamber and defining stations for receiving articles to be heated and a drive mechanism for producing rotation of the turntable. A control circuit controls energization of the source in response to signal outputs from temperature responsive sensors positioned in the heating stations. The rotary coupling includes a stationary portion mounted on the housing and having stationary contacts connected to the control circuit and a rotary portion mounted on the turntable and having rotary contacts connected to the sensors and slidably engaging the stationary contacts during rotational movement of the turntable. The invention facilitates the retrieval of signal information from temperature sensors moving within a microwave oven chamber.

A featured embodiment of the invention includes an electrical signal multiplexer mounted within the oven chamber and having an input connected to receive output signals from all the sensors and an output connected to the rotary contacts and adapted to sequentially transmit thereto all of the output signals in a predetermined sequence. The multiplexer increases the signal capacity of the rotary coupling assembly.

According to one feature of the invention, the multiplexer is retained in an electrically conductive can, an output surface portion of which is covered with a dielectric material and an electrically conductive skirt adjacent thereto. Microwave energy is shielded by the conductive can and dissipated by the capacitive block formed by the can, the dielectric material and the conductive skirt thereby preventing interference with the multiplexer signals.

According to another feature of the invention, the rotary coupling portion comprises an insulator column extending through a wall portion of the housing and having an outer surface supporting the rotary contacts that comprise longitudinally spaced apart rings and the stationary coupling portion comprises an insulator block supporting the stationary contacts and having a cylindrical opening receiving the insulator column. The stationary contacts include a plurality of spring contacts arranged in pairs, the spring contacts forming each pair straddling and engaging a different one of the ring contacts and being electrically interconnected. This arrangement establishes efficient electrical coupling and the redundant pairs of spring contacts prevent loss of signal in response to the inadvertent misalignment or vibration of the various individual components.

According to still another feature of the invention, the rotary turntable includes a centrally located post, a shaft coaxially and slidably received thereby, means keying the shaft to the post for rotation therewith, and a release mechanism operable to permit relative axial movement between the post and the shaft. After actuation of the release mechanism the insulator column can be withdrawn from the insulator block permitting removal of the entire turntable assembly from the oven chamber. Reassembly of the components is simplified by a conically shaped terminal portion on the insulator column that engages the pairs of spring contacts during movement of the column into the insulator block.

DESCRIPTION OF THE DRAWINGS

These and other objects and features of the invention will become more apparent upon a perusal of the following description taken in conjunction with the accompanying drawings wherein:

FIG. 1 is a schematic perspective view of a microwave oven according to the invention;

FIG. 2 is a schematic front view, partially in cross section, of one heating station of a turntable illustrated in FIG. 1;

FIG. 3 is a schematic side view, partially in cross section of the heating station illustrated in FIG. 2;

FIG. 4 is a schematic cross-sectional view of a temperature sensor illustrated in FIGS. 2 and 3;

DESCRIPTION OF THE PREFERRED EMBODIMENT

Figure 5:
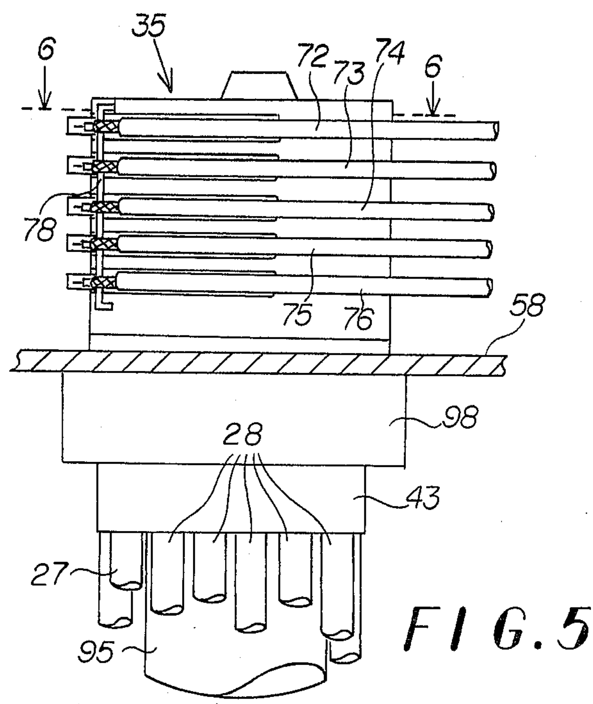
FIG. 5 is a schematic elevational view of a rotary electrical coupling shown in FIG. 1.

FIG. 1 illustrates a microwave heating apparatus 11 constructed in accordance with the present invention. A housing 12 defines an oven chamber 13, access to which is provided by a door 14'. Rotatably supported within the chamber 13 is an article supporting turntable assembly 14 that is coupled to a rotary drive mechanism 15. A microwave source 16 transmits into the oven chamber 13 radiant energy for heating articles retained therein. Disposed on a control panel 17 of the housing 12 is a display 18, a plurality of oven control buttons 19 and a program card insert slot 21. Interconnected with the control panel 17, the microwave source 16, and the drive mechanism 15 and a dc power supply 22 is an oven control printed circuit 23. The foregoing portions of the microwave unit 11 are used in commercially available microwave ovens.

Retained by the turntable 14 is a control station 24 and a plurality of annularly distributed auxiliary stations 26 each adapted to receive an article to be heated within the chamber 13. Positioned within the control station 25 is a temperature responsive control sensor 27 while a temperature responsive safety sensor 28 is positioned in each of the auxiliary stations 26. A safety control circuit 31 is electrically coupled to an alarm horn 32, an alarm light 33, a reset switch button 34 and the oven control circuit 23. Electrical signals from the sensors 27, 28, respectively, are fed out of the chamber 13 to the oven control circuit 23 and the safety control circuit 31 via a rotary electrical coupling assembly 35. The heating stations 25, 26; the sensors 27, 28; the rotary coupling assembly 35 and the safety control circuit 31 are described in detail below.

Referring now to FIGS. 2 and 3, there are shown in greater detail the control station 25 and the control sensor 27. The auxiliary stations 26 and the safety sensors 28, respectively, are structurally identical to the control station 25 and the control sensor 27 and therefore will not be further described. Forming the control station 25 is a tray 37 having a lower end retained by a base portion 36 of the turntable 14 and an upper end retained by a top portion 38 thereof. The control sensor 27 includes a horizontally oriented terminal portion 41 juxtaposed a central portion of the tray 37. Extending from the upper portion of the tray 37 is a hook 39 that retains an article 40 to be heated. In preferred use of the invention, the article 40 would consist, for example, of a flexible plastic bag (as shown) containing a frozen substance to be administered intravenously. When positioned on the hook 39 the bag 40 overlays and engages the terminal portion 41 of the sensor 27 so as to be in good thermal contact therewith. As shown in FIG. 3, the terminal portion 41 of the sensor 27 has an elongated cross section so as to establish a planar surface substantially parallel to and in intimate contact with the bag 40 thereby improving heat transfer therebetween. As also shown in FIG. 3, the tray 37 is supported at a small angle of, for example, six degrees with respect to vertical. That angle can be increased if increased rates of heating are desired for fewer stations.

As shown in FIG. 4, the control sensor 27 includes an elongated tube comprising the horizontal portion 41 and a vertical portion 42 that extends out of a sealed metal can 43 that also accommodates the safety sensors 28 (FIG. 5). Extending through the tube 41, 42 is a cable 44 composed of a pair of insulated signal wires 45, 46, a braided conductive shield 47 and an insulator cover 48. The outer ends of the signal wires 45, 46 are connected to the terminals of a thermistor 49 while the inner ends thereof are connected to an electrical circuit retained within the can 43 as described below. Enclosing the outer ends of the wires 45, 46 and the thermistor 49 is an electrical insulator tube 51. The volume between the braided shield 47 and the horizontal tube portion 41 is filled with potting material such as silver epoxy having high thermal conductivity so as to establish good heat transfer between the tube portion 41 and the thermistor 49.

Heat transfer between the bag 40 (FIG. 2) and the thermistor 49 is maximized by the high thermal conductivity of the tube portion 41 and the potting compound 52. However, direct microwave energy heating of the sensor 27 is minimized by the tube 41, 42 that functions as a microwave energy shield. Preferably, the tube 41, 42 is formed of a highly conductive material such as brass and plated to an extremely fine finish with a very low resistive material such as silver. In this way surface conductivity is maximized and microwave heating of the sensor 27 minimized because of the skin effect phenomenon. In addition, the length of the sensor 27 is selected so as to establish therefor a detuned antenna condition at the microwave frequencies transmitted by the source 16. Such detuning further limits microwave heating of the sensor 27.

During assembly of the sensor 27, the end of the braided shield 47 is withdrawn to expose the ends of the signal wires 45, 46 which are attached to opposite terminals of the thermistor 49. The insulator tube 51 then is positioned over the thermistor 49 and covered with the previously withdrawn portion of the braided shield 47. Thus prepared, the thermistor assembly is inserted through the open end of the tube portion 42 until reaching the position within the tube portion 41 illustrated in FIG. 4. An electrically and thermally conductive potting compound 52 such as silver epoxy then is faced through an opening 55 to completely fill the tube portion 41. In addition to providing a mass for transferring heat between the bag 43 and the thermistor 49, the material 52 seals the opening 55 to establish complete microwave shielding of the components within the tube 41.

Figure 6:
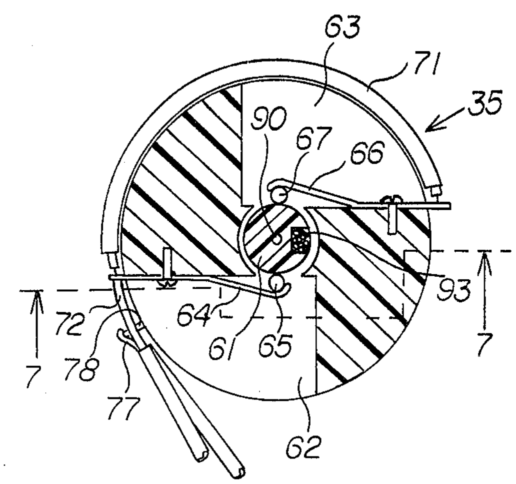
FIG. 6 is a schematic cross-sectional view taken along the lines 6—6 of FIG. 5.

Referring now to FIGS. 5–8, there are shown further details of the rotary feedthrough assembly 35. A cylindrical insulator block 57 is mounted on a wall option 58 of the housing 12 that closes the top of the oven chamber 13. Extending axially through the cylindrical block 57 is an opening 59 that accommodates a column assembly 61 the lower end of which extends through the wall portion 58 and is attached to the can 43. A plurality of spaced apart, radial slots 62 enter one longitudinal surface portion of the block 57. Radially projecting into an opposite longitudinal surface portion of the block 57 are a plurality of spaced apart slots 63. Although only one slot 63 is shown in FIG. 6, it should be understood that the block 57 contains a plurality of slots 63, one radially aligned with each of the slots 62. Retained by a screw in each of the slots 62 is a resilient conductive blade 64 having an outer portion projecting beyond the outer surface of the block 57 and an inner contact 65 spring loaded against the column 61. Similarly, each of the slots 63 retains a resilient conductive blade 66 having an outer portion extending out of the block 57 and an inner contact 67 spring loaded against the column 61. The portions of each aligned pair of the blades 64, 66 that extend out of the block 57 are electrically connected by insulated conductors 71. In addition, the outer terminal portion of each of the blades 64 is connected to a different insulated signal wire 72–76 (FIG. 5). round shields 77 for all of the signal wires 72–76 are electrically connected to a bus wire 78 extending longitudinally of the block 57 and having opposite ends inserted into receiving openings therein.

Figure 8:
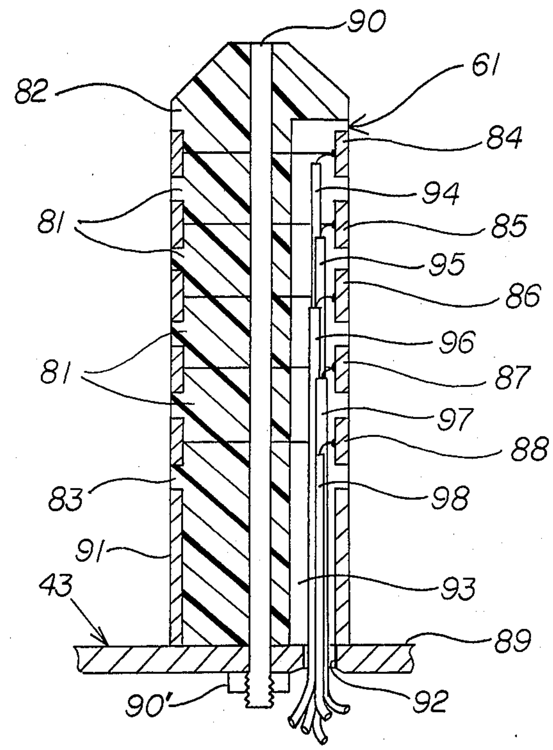
FIG. 8 is a schematic cross-sectional view through a center column of the rotary coupling shown in FIGS. 5-7.

Referring now to FIG. 8, there are shown details of the central column 61 which includes a stacked plurality of identical insulator discs 81 straddled by a conically shaped insulator 82 and an elongated cylindrical insulator 83. Circumferential recesses are formed along upper and lower edges of the discs 81, a lower edge of the conically shaped insulator 82 and an upper edge of the elongated insulator 83. Adjacent pairs of these recesses form annular channels each conforming to and receiving a ring contact 84–88 and a metal cylinder 91 encapsulates the lower portion of the elongated insulator 83. Each of the contact rings 84–88 is positioned so as to be engaged by a different pair of the spring loaded contacts 65, 67. Press fitted through central apertures in the discs 81–83 is an alignment rod 90 that also extends through an upper wall 89 of the can 43 and is secured thereto by a nut 90'. Also formed in each of the discs 81–83 is a longitudinal slot, all of which are aligned to provide a longitudinal channel 93 through the column assembly 61. Extending through the channel 93 and an opening 92 in the wall portion 89 are a plurality of electrical leads 94–98, one electrically connected to each of the contact rings 84–88. Opposite ends of the leads 94–98 are connected to electrical circuitry in the can 43 as described below. Thus, the leads 94–98 are individually connected, respectively, to the signal wires 72–76 (FIG. 5) via the ring contacts 84–88 and the blade contacts 64, 66.

Referring again to FIGS. 5 and 7, there is depicted in greater detail the can 43 which, as described below, houses electronic circuitry connected between the sensors 27, 28 and the rotary coupling 35. As shown, the can 43 is supported by a shaft 95' and in turn supports the central column 61. To limit the entry of microwave energy, the walls 96' of the can 43 are preferably formed of a good electrically conductive material such as brass and plated to a fine finish with a highly conductive material such as silver to establish minimum surface resistance. In addition, the side walls 96 of the can 43 are covered with a dielectric material 97', for example Teflon tape, that is separated by a small air gap from a cylindrical metallic skirt 98' secured to the wall portion 58 by screws 99. Together, the dielectric coating 97' and straddling conductive skirt 98 and side walls 96 form a capacitive block that serves to dissipate microwave energy preventing its entry into the can 43. Further isolation is provided by an annular, energy absorbing disc 101 positioned between the can 43 and the wall portion 58 and an annular, energy absorbing disc 102 positioned between the wall portion 58 and the rotary coupling 35. The discs 101 and 102 are formed of a suitable microwave energy absorbing material such as Eccosorb (SFT-2.5) sold by Emmerson and Cummings of Canton, Mass.

Figure 7:
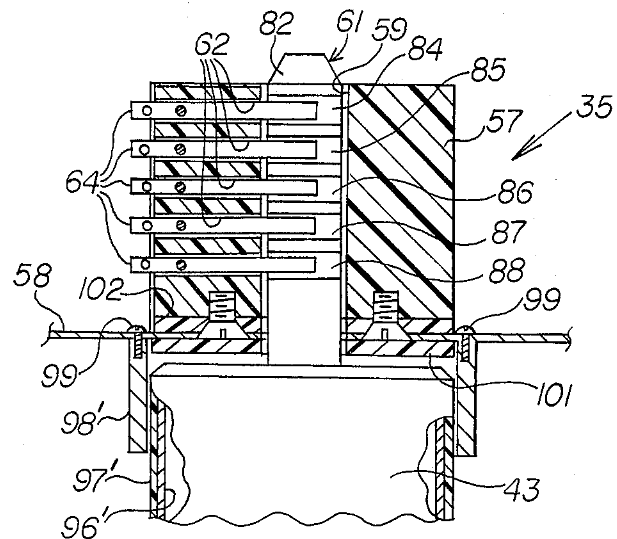
FIG. 7 is a schematic cross-sectional view taken along the lines 7—7 of FIG. 6.
Figure 9:
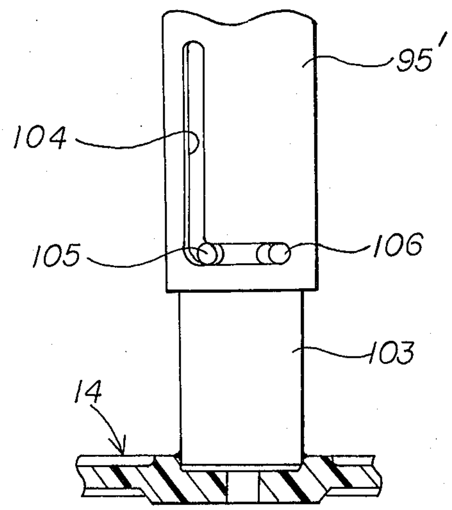
FIG. 9 is a schematic view illustrating assembly details of the turntable and rotary coupling shown in FIG. 1.

Illustrated in FIG. 9 is the manner in which the can 43 and the components associated therewith are supported on the turntable 14 within the chamber 13. The hollow shaft 95' supporting the can 43 is slidably received over a post 103 extending centrally from the turntable 14. Secured to the post 103 and extending through a base portion of an L-shaped slot 104 in the shaft 95' is a pin 105 that prevents relative vertical movement therebetween. A second pin 106 is removably received by a hole in the post 103 and also extends through the base portion of the slot 104. When in position, the pin 106 prevents relative rotational movement between the shaft 95' and the column 103 that would align the pin 105 with the upright portion of the slot 104. However, upon removal of the pin 106, such relative movement can occur allowing the shaft 95' to move downwardly on the post 103 as the pin 105 is received by the upright portion of the slot 104. The relative vertical movement between the post 103 and the shaft 95 is sufficient to permit withdrawal of the support can 43 and column 61 from both the rotary coupling assembly 35 and the skirt member 98 (FIG. 7). Thus, those components together with the turntable 14 can be removed from the oven chamber 13 through the door 14. During reassembly, the conically shaped insulator 82 facilitates centering of the column 61 during entry into the coupling assembly 35 and also functions to gently separate the spring loaded contacts 65 and 67 (FIG. 6) as the column 61 enters the central opening 59 in the insulator block 57.

Figure 10:
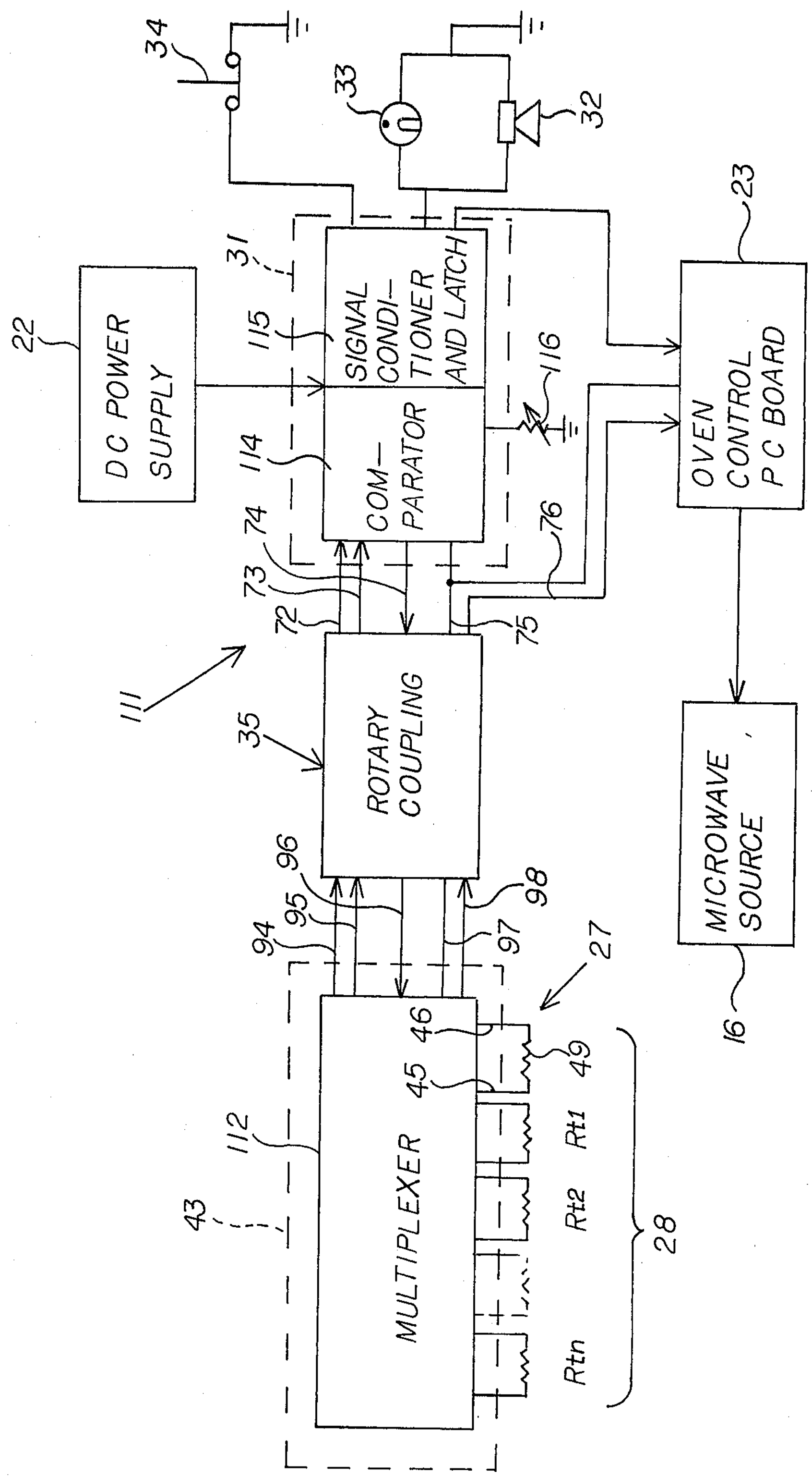
FIG. 10 is a schematic block circuit diagram of an electrical control circuit for the microwave oven shown in FIG. 1.

FIG. 10 depicts in block diagram form an electrical circuit 111 for controlling operation of the microwave oven 11. Included in the control circuit 111 are a multiplexer 112 and the safety control circuit 31 that includes a comparator section 114 and a signal conditioner and latch section 115. A variable resistor 116 provides an adjustable reference voltage for the comparator 114. The multiplexer 112 is housed in the can 43 (FIGS. 5 and 7) and receives on lines 45 and 46 the output of the control thermistor 49 in the control sensor 27. Also received by the multiplexer 112 are the outputs of thermistors $R_{t1}$, $R_{t2}$... $R_{tn}$ retained by the safety sensors 28 (FIG. 1). Connecting the multiplexer 112 to the safety circuit 31 is the rotary coupling 35. The safety circuit 31 receives power from the supply 22 and is connected to energize the horn 32 and the light 33 and to be released from a latched condition by the reset button switch 34. Receiving signals from both the signal conditioner section 115 and the rotary coupling 35 is the oven control circuit 23 that in turn controls energization of the microwave source 16.

OPERATION

During operation of the microwave unit 11, articles to be heated are positioned in the stations 25, 26 within the oven chamber 13. In specific applications, the articles would consist of flexible plastic bags 40 filled with a frozen substance suitable after thawing for intravenous administration. Although any of the stations 26 can remain unoccupied by a frozen bag, a bag should always be positioned in the control station 25 before each thawing cycle. For that reason, the control station 25 is clearly distinguished from the auxiliary stations 26 by a label 121. In addition, the filled volumes of all bags in a given run should be substantially equal and their contents should possess substantially similar thawing characteristics. After the turntable 14 has been filled with the number of bags required, the door 14 is closed, a suitable program card is inserted into the slot 21 and the oven control buttons 19 are operated in a conventional manner to energize the microwave source 16 and begin a thawing cycle. As the thawing process proceeds, the thermistor retained by each sensor 27, 28 in an occupied station exhibits a resistance proportional to the temperature of the bag with which it is in thermal contact. Conversely, the thermistors retained by sensors in unoccupied stations reflect the ambient temperature in that station. The temperature indicating signal from the control sensor 27 on the lines 45, 46 is fed through the can 43 directly to the leads 97, 98 via the rotary coupling 35 and output lines 75, 76 to the oven control circuit 23. However, the individual outputs of the safety sensors 28 are received by the multiplexer 112 that continuously transmits those signals over the leads 94, 95 in a predetermined sequence. The multiplexed signals are fed through the rotary coupling 35 and over the output lines 72, 73 to the comparator section 114. DC supply voltage is received by the multiplexer 112 from the safety circuit 31 via the line 74, the rotary coupling 35 and the lead 96. A common for both the dc supply and the output of the control sensor 27 is provided by the line 75, the lead 97 and the rotary coupling 35. The oven control circuit 23 is programmed to monitor a thawing operation and control energization of the source 16 in response to signal information from the control sensor 27. When that signal information indicates that substantially the entire content of the bag in the control station 25 has reached a fully thawed temperature threshold of, for example, 25° C., the oven circuit 23 terminates operations. At that time, the bags retained in any of the auxiliary stations 26 will have reached substantially the same temperature because of the even distribution of microwave energy established by the rotating turntable 14. At the conclusion of a defined cycle, the door 14 can be opened and the thawed bags removed and used as desired.

Assume, however, that a bag in one of the auxiliary stations 26 inadvertently reaches a predetermined maximum safe temperature threshold of, for example, 50° C. Temperature levels above that threshold could either damage the bag's fluid content or induce bursting thereof. Such a situation can result from various circumstances such as, for example, if an auxiliary station 26 retains at the initiation of a thawing cycle a bag that is thawed or partially thawed, a bag of lesser volume than the bag retained in the control station 25, or a bag filled with a substance having a substantially different thermal characteristic than the bag retained in the control station 25. Upon reaching the predetermined unsafe temperature, the safety sensor 28 associated with that bag produces via the multiplexer 112; the data wires 94, 95; the rotary coupling 35 and the output leads 72, 73 a signal voltage below a reference voltage established by the adjustable resistor 116 within the comparator 114. In response thereto, the comparator section 114 and signal conditioner and latch section 115 produce an output to the oven circuit 23 inducing deenergization of the microwave source 16. In addition, the signal conditioner section 115 energizes the horn 32 and the light 33 providing both audible and visible indications that the predetermined safe temperature limit has been exceeded. Thawing operations can be resumed only after the overheated article is removed, the overheated sensor cools below the threshold point and the reset button 34 is manually operated to eliminate the latch condition existing in the circuit section 115.

An important feature of the invention prevents the safety sensors 28 in unoccupied auxiliary stations 26 from reaching a temperature that would cause oven shutdown. This feature permits use of the oven unit 11 with the turntable 14 filled to less than full capacity. Referring again to FIG. 4, the mass provided by thermally conductive potting material 52 functions as a heat sink that disperses the limited amount of heat that is generated by microwave energy present on the surface of the shield portion 41. Consequently, the mass 52 in an unoccupied station 26 and the thermistor retained thereby will not reach oven shutdown temperature during normal operations. Conversely, in the absence of a frozen bag in the control station 25, the mass 52 in the control sensor 27 is selected so as to be heated by microwave energy to a temperature above that required to normally terminate a thawing operation. Thus, in the event that a frozen bag is not positioned in the control station 25, the control sensor 27 will quickly reach a temperature that will induce the oven control circuit 23 to react as if a regular thawing cycle has been completed. A normal cycle can proceed only after an operator has discovered the problem and positioned a frozen bag in the control station 25.

Obviously, many modifications and variations of the present invention are possible in light of the above teachings. For example only, although a prefered use of the invention has been described, it will be obvious that the oven 11 can be used to safely heat batches of articles other than those specifically mentioned. It is to be understood, therefore, that the invention can be practiced otherwise than as specifically described.

What is claimed is:

1. Microwave oven apparatus comprising:

housing means defining an oven chamber;

door means providing access to said chamber;

source means energizable to transmit microwave energy into said chamber;

support means rotatably mounted within said chamber and defining a plurality of heating stations for receiving articles to be heated;

drive means energizable to produce rotation of said support means;

temperature responsive sensor means mounted on said support means for rotation therewith, said sensor means comprising a plurality of temperature responsive sensors each positioned and arranged to sense the temperature of an article retained in a different one of said stations;

control circuit means mounted outside said chamber and adapted to control energization of said source means in response to signal output from said sensor means;

a rotary coupling assembly electrically connecting said circuit means to said sensor means, said coupling assembly comprising a substantially stationary portion mounted on said housing means and having substantially stationary contact means connected to said control circuit means and a rotary portion mounted on said support means and having rotary contact means connected to said sensor means, said rotary contact means slidably engaging said stationary contact means during rotational movement of said support means; and multiplexer means mounted on said support means within said chamber and having an input connected to receive output signals from all of said sensors, said multiplexer means having an output connected to said rotary contact means and adapted to sequentially transmit thereto all of said output signals in a predetermined sequence.

2. Apparatus according to claim 1 including an electrically conductive can completely enclosing said multiplexer means so as to provide microwave energy shielding therefor.

3. Apparatus according to claim 2 including dielectric means covering an outer surface portion of said can and an electrically conductive skirt means disposed adjacent to said dielectric means; said can, said dielectric means, and said skirt means forming a capacitive block that dissipates microwave energy transmitted by said source.

4. Apparatus according to claim 2 wherein said rotary contact means comprises a plurality of electrically isolated rotary contacts each connected to a different output terminal of said multiplexer, and said stationary contact means comprises a plurality of electrically isolated stationary contacts, each slidably engaging one of said rotary contacts.

5. Apparatus according to claim 4 wherein said rotary portion comprises a cylindrical insulator column extending through a wall portion of said housing and with an outer surface supporting said rotary contacts that comprise longitudinally spaced apart ring contacts; and said stationary portion comprises an insulator block supporting said stationary contacts and having a cylindrical opening receiving said insulator column.

6. Apparatus according to claim 5 wherein said stationary contacts comprise a plurality of spring contacts arranged in pairs, the spring contacts forming each said pair straddling and engaging a different one of said ring contacts and being electrically connected by conductor means.

7. Apparatus according to claim 6 wherein said rotary support comprises a centrally located post, a shaft coaxially and slidably received by said post, a means keying said shaft to said post for rotational movement therewith, and release means operable to permit relative axial movement between said post and said shaft so as to allow withdrawal of said column from said insulator block.

8. Apparatus according to claim 7 wherein said column comprises a conically shaped terminal portion adapted to engage said pairs of spring contacts during movement of said column into said insulator block.

9. Microwave oven apparatus comprising:

housing means defining an oven chamber;

door means providing access to said chamber;

source means energizable to transmit microwave energy into said chamber;

support means rotatably mounted within said chamber and defining a plurality of heating stations for receiving articles to be heated;

drive means energizable to produce rotation of said support means;

temperature responsive sensor means mounted on said support means for rotation therewith, said sensor means comprising a plurality of temperature responsive sensors each positioned and arranged to sense the temperature of an article retained in a different one of said stations;

control circuit means mounted outside said chamber and adapted to control energization of said source means in response to signal output from said sensor means; and a rotary coupling assembly electrically connecting said circuit means to said sensor means, said coupling assembly comprising a substantially stationary portion mounted on said housing means and having a plurality of substantially stationary contact connected to said control circuit means and a rotary portion mounted on said support means and having a plurality of rotary contacts each connected to one of said sensor means and slidably engaging one of said stationary contacts during rotational movement of said support means and wherein said rotary portion comprises a cylindrical insulator column extending through a wall portion of said housing and with an outer surface supporting said rotary contacts that comprise longitudinally spaced apart ring contacts; and said stationary portion comprises an insulator block supporting said stationary contacts and having a cylindrical opening receiving said insulator column.

10. Apparatus according to claim 9 wherein said stationary contacts comprise a plurality of spring contacts arranged in pairs, the spring contacts forming each said pair straddling and engaging a different one of said ring contacts and being electrically connected by conductor means.

11. Apparatus according to claim 9 wherein said rotary support comprises a centrally located post, a shaft coaxially and slidably received by said post, a means keying said shaft to said post for rotational movement therewith, release means operable to permit relative axial movement between said post and said shaft so as to allow withdrawal of said column from said insulator block.

12. Apparatus according to claim 11 wherein said column comprises a conically shaped terminal portion adapted to engage said pairs of spring contacts during movement of said column into said insulator block.

* * * * *